United States Patent [19]

Small et al.

[11] 4,017,262

[45] Apr. 12, 1977

[54] CHROMATOGRAPHIC APPARATUS FOR ANALYSIS OF IONIC SPECIES

[75] Inventors: Hamish Small; Timothy S. Stevens, both of Midland, Mich.

[73] Assignee: The Dow Chemical Company, Midland, Mich.

[22] Filed: Sept. 8, 1975

[21] Appl. No.: 611,107

Related U.S. Application Data

[62] Division of Ser. No. 386,261, Aug. 6, 1973, Pat. No. 3,925,019.

[52] U.S. Cl. .......................... 23/253 R; 73/61.1 C; 210/284; 210/294

[51] Int. Cl.[2] ................ G01N 27/08; G01N 31/04; G01N 31/08

[58] Field of Search ................. 23/230 R, 253 R; 210/24, 25, 31 C, 37, 38, 284, 294; 73/61.1 C

[56] References Cited

UNITED STATES PATENTS

| | | | |
|---|---|---|---|
| 2,422,054 | 6/1947 | Tiger | 210/25 |
| 2,938,868 | 5/1960 | Carlson | 210/25 |
| 3,382,034 | 5/1968 | Kraus | 210/24 X |
| 3,686,117 | 8/1972 | Lauer | 210/31 C |
| 3,694,369 | 9/1972 | Orlandini | 210/38 |

Primary Examiner—Joseph Scovronek
Assistant Examiner—Sidney Marantz
Attorney, Agent, or Firm—Glenn H. Korfhage; Daniel DeJoseph

[57] ABSTRACT

Apparatus and method for chromatographic quantitative analysis of a solution containing a plurality of species of cations. A sample of the solution is added to a first ion exchange resin bed containing cation exchange resin and eluted therefrom with a solution of developing reagent consisting of either $AgNO_3$ or $BaCl_2$, chromatographic separation of the cationic species being achieved as elution proceeds. The effluent from the first ion exchange resin bed is passed through a second ion exchange resin bed containing anion exchange resin in a form appropriate to the precipitation of whichever metal ion is provided by the developing reagent, i.e., chloride or sulfate forms. As elution proceeds the cations exit from the second ion exchange bed without destroying the ionic separation achieved in the first ion exchange resin bed. Each separated cationic species is quantitatively sensed by a detector such as a conductivity cell on exiting from the second ion exchange resin bed.

4 Claims, 1 Drawing Figure

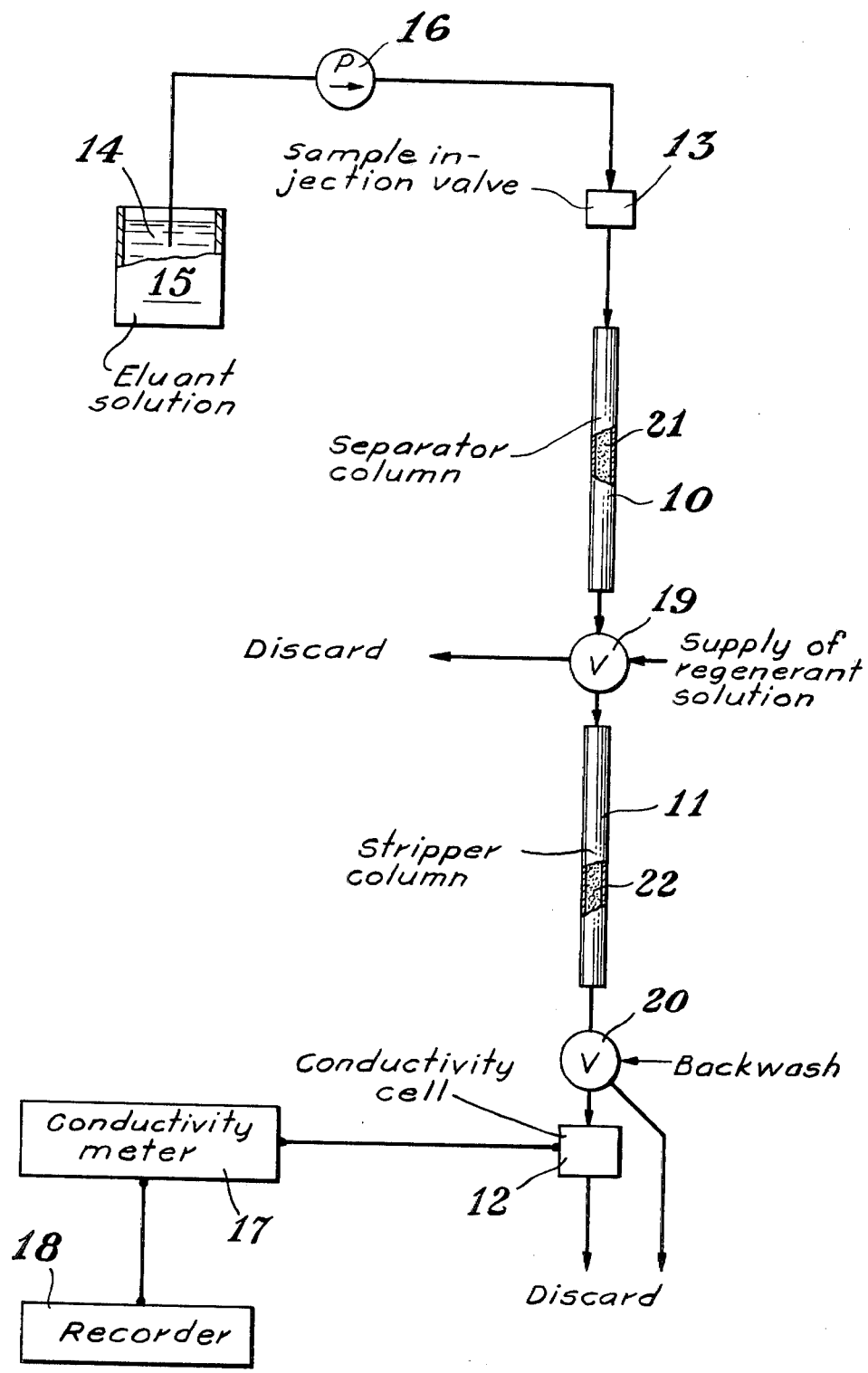

CHROMATOGRAPHIC APPARATUS FOR ANALYSIS OF IONIC SPECIES

CROSS REFERENCE TO RELATED APPLICATIONS

This is a divisional application of copending application Ser. No. 386,261 filed Aug. 6, 1973 U.S. Pat. No. 3,925,017.

In a copending application of Hamish Small and William C. Bauman, Ser. No. 386,260 fled Aug. 6, 1973 there is U.S. Pat. No. 3,920,397 described a method for chromatographic quantitative analysis of ionic species in solution wherein the solution is passed first through a separator ion exchange resin bed means and then through a stripper ion exchange resin bed means and then through a detector such as a conductivity cell and associated readout means. Chromatographic separation is carried out in the separator bed and in the stripper bed the developing reagent used in the eluant solution is acted upon by an ion exchange resin so that the developing reagent does not reach the detector in highly ionized form along with the separated ionic species being analyzed. For example, the developing reagent is converted to a weakly dissociated molecule such as water or is captured on ion exchange sites.

In a copending application of Timothy S. Stevens, Ser. No. 386,262, filed, Aug. 6, 1973, U.S. Pat. No. 3,926,559 there is described a method for chromatographic quantitative analysis of cationic species in solution, particularly the more tightly bound cations, wherein cationic species such as amines are maintained in stable ionic form wherein the eluant solution employed consists of a mixture of a metal ion capable of moving the more tightly bound cations off a cation exchange resin and sufficient hydronium ion to assure stabilization of ions such as protonated amines so that chromatographic separation is possible upon a separator cation exchange resin bed. Use of such mixed developing reagent as the eluant solution is made possible by the employment of two separate stripper anion exchange resin beds in series, the first bed containing an anion exchange resin in a form suitable for precipitation of the metal ion used in the developing reagent and the second bed containing an anion exchange resin in the hydroxide form whereby all of the hydronium ion utilized is neutralized before the solution of separated cations under determination exit from the third chromatographic column and are directed to a detector such as a conductivity cell.

In a copending application of Hamish Small and Timothy S. Stevens, Ser. No. 386,263, filed Aug. 6, 1973, U.S. Pat. No. 3,918,906, there is disclosed the determination of the total ionic content of an aqueous sample solution on utilizing ion exchange method in which the sample solution is added to a cation exchange resin in easily elutable cation form and the easily elutable cations displaced are eluted from the column with water, the effluent being passed to an anion exchange resin which is in easily elutable anionic form, usually the hydroxide form. In the latter column all the anionic species in the sample are exchanged for a single anion. The effluent from the second resin bed, consisting entirely of a single ion pair species, viz., the preselected cation and the preselected anion, in water solution, is passed through a conductivity cell. Readout means associated with the conductivity cell indicate the number of equivalents of the single ion pair species corresponding to the number of equivalents of ionically dissociated compounds in the predetermined volume of sample solution.

In another copending application of Timothy S. Stevens and Hamish Small, Ser. No. 386,264, filed Aug. 6, 1973, U.S. Pat. No. 3,920,398 there is described a chromatographic method of separating and quantitatively detecting water soluble carboxylic acids and their salts. The carboxylic acids in aqueous solution substantially devoid of other ionic materials are passed through a cation exchange resin in the hydrogen ion form and eluted with water to obtain chromatographic separation. The effluent from the resin bed is led to a conductivity cell having associated readout means indicating passage of the separated organic acids through the conductively cell. Interfering ionic substances if present are removed as by precipitation or in the case of the alkali metal halides, the solution is first passed through a cation exchange resin in the silver ion form whereupon the halide is precipitated as silver halide and an equivalent amount of alkali metal ions are captured at the ion exchange sites.

In an additional copending application of Timothy S. Stevens and Hamish Small, Ser. No. 386,265, filed Aug. 6, 1973, U.S. Pat. No. 3,915,642, there is described apparatus and method for rapidly and accurately quantitatively measuring the quantity of a given ion in aqueous solution in the presence of a plurality of counter valent ions, using ion exchange techniques and a conductivity cell as detector.

BACKGROUND OF THE INVENTION

1. Field of the Invention

The invention relates to apparatus and method for chromatographic quantitative analysis of a mixture of cationic species of ionized material in solution utilizing a cation exchange bed to resolve the cations to be analyzed and subsequently, and in series, an anion exchange bed to capture the cations of the developing reagent used while passing the separated cations on to a single common detector whereby simple rapid analysis is carried out.

2. Description of the Prior Art

There is a constant and ever increasing demand for analysis of ionic species in aqueous solution or other highly polar medium, particularly for inorganic species. This demand has become more prominent of late with the emphasis on water monitoring in connection with pollution control. Chromatographic methods of analysis have a particular appeal, especially from the point of view of automated monitoring, but no chromatographic technique has ben developed heretofore for inorganic species that enjoys the same widespread use as does vapor phase chromatography for organic species. Moreover, this situation has prevailed despite the well-known ability of ion exchange resins to separate ionic species whether they be cationic or anionic in nature. The probable reason for this appears to be as follows. At least two very necessary prerequisites determine the utility of a chromatographic method: (1) separation of the ionic species by some means in the chromatographic column so that they appear at different times in the effluent, i.e., the species are resolved; (2) a convenient means of continuously and accurately analyzing for the species in the effluent, the means being universally applicable for every species contemplated.

The first prerequisite is quite well satisfied by the known ion exchange resins. For instance, it is a simple matter to obtain excellent separations of complex mixtures of cations or anions merely by eluting them through an ion exchange bed with an appropriate electrolyte serving as eluant or developing reagent.

The problem, however, is the inability, except in quite special cases, to satisfy the second prerequisite. As a rule, it simply is not possible to distinguish the ions eluting from the column from the more concentrated background consisting of developing reagent used to develop the chromatogram. In some instances it has been possible to use spectrophotometric detectors to distinguish a wide variety of ions, mainly organic ions. However, in the case of many ions, particularly for inorganic ions such as the ions of lithium, sodium, potassium, calcium, chlorine, bromine, iodine, and, the ammonium, nitrate, nitrite, sulfate and phosphate ions, spectrophotometric methods have not been widely employed.

The use of two ino exchange resin beds in series for the demineralization of water is well-known. Typically, the first bed removes cations and the second bed removes anions to achieve a grade of water sometimes approaching the quality of distilled water as to mineral content and conductivity In such demineralization operations, the mineral ions, both cations and the paired anions, are captured and held until the respective resin beds are loaded enough so that a substantial proportion of ions "break through" the ion exchange beds whereupon they are detected by a conductivity meter or by a "hardness" test. At this stage operations are either stopped or switched to an alternate set of beds and both ion exchange resin beds are subjected to respective separate backwashing and regeneration procedures wherein the cation exchange resin bed is soaked in strong mineral acid while the anion exchange resin bed is soaked in strong base, and each thoroughly rinsed with tap water whereupon the demineralizing equipment is ready for further service. During the demineralizing operations there is not elution with an eluant, or developing reagent, there is no development of a chromatographic separation, and no analysis, much less quantitative analysis of separated ionic species.

SUMMARY OF THE INVENTION

It has now been discovered that chromatographic quantitative analysis of a plurality of cationic species in aqueous sample solution is readily and expeditiously carried out upon adding a predetermined amount of the sample solution to a cation exchange resin bed means, the resin bed means being charged with a cation exchange resin, and chromatographically separating the plurality of species of cations or elution of the cation species from the resin bed means with an aqueous solution of a developing reagent selected from the group consisting of $AgNO_3$ and $BaCl_2$, the cation exchange resin and the developing reagent being preselected to cooperatively facilitate chromatographic separation of said cation species; passing the effluent from the cation exchange resin bed means through an anion exchange resin bed means containing an anion exchange resin in a form capable of precipitating whichever metal ion is used as the developing reagent, the form being selected from the group consisting of chloride and sulfate ion form, the total exchange capacity of anion exchange resin being at least sufficient to substantially precipitate all of the metal ion contained in the solution of developing reagent used for elution, the nature of the anion exchange resin and the configuration of the bed thereof being preselected to not destroy the said chromatographic separation; and passing the effluent from the anion exchange resin bed means through a common detector means and quantitatively detecting each of said separated ion species, respectively. The method is of particuar advantage in separation of cations, such as the alkaline earth metal ions which are more tightly bound to the cation exchange resin and elute off too slowly for practical analytical work.

The present apparatus includes two chromatographic columns and a detector such as a conductivity cell connected in series by liquid conduit means, means for adding liquid sample solution and solution of developing reagent to the first column and readout means associated with the detector. Further, the first chromatographic column is charged with a cation exchange resin, preferably a high performance, low capacity ion exchange resin and the second chromatographic column is charged with an anion exchange resin in either the chloride or the sulfate from so as to precipitate the developing reagent. It is essential that the anion exchange resin in the second chromatographic column has sufficient total exchange capacity to precipitate all of the metal ion in the development reagent solution used to complete a chromatographic analysis in its entirely and more preferably to permit the completion of at least five, and even more preferably at least 20, chromatographic determinations before it is necessary to replace or regenerate the anion exchange resin. Generally the anion exchange resin in the stripper bed should have a total exchange capacity at least 50 and preferably at least 500 or more times the total exchange capacity of the cation exchange resin in the separator bed.

BRIEF DESCRIPTION OF THE DRAWING

The single FIGURE of the drawing is a schematic representation of an embodiment of the apparatus of the inventon showing in series a reservoir of eluant solution, a pump, a special injection valve or other sample injection device, a chromatographic column charged with a cation exchange resin and a second chromatographic column charged with an anion exchange resin in the chloride or sulfate form, the columns being used in series and followed by a detector such as a conductivity cell having associated readout means.

FURTHER DESCRIPTION OF THE INVENTION

The present method and apparatus are well adapted for the rapid and automated analysis of a great variety of cationic species present in aqueous solution, but is of particular advantage in analyzing and separating groups of cations that are more tightly bound or held to the ion exchange resin than are, for example, the alkali metal cations. The cations of the alkaline earth metals, for example, as a group are relatively tightly held by cation exchange resins and elution with a developing reagent such as aqueous hydrochloric acid is not only relatively slow but tends to bring these cations off in smeared out concentration peaks of ow peak height above the base line. As a consequence, sensitivity is reduced. These problems have been solved according to the present invention by utilizing a solution of developing reagent that is more effective in competing for the ion exchange sites and thus moving the cations of interest off the column in a shorter period of time and with sharply defined peaks providing for good sensitivity of detection. The method is effective for the separation of any of the alkaline earth metal cations from the other alkaline earth metal cations as well as from other cations, especially the alkali metal cations. It is also effective, generally, in effecting separations among either cations less tightly bound than the alkaline earth metal ions, such as the alkali metal cations. In any event, the cations subject to separation by the instant method must be readily movable off the cation exchange resin and separable chromatographically by the use of the developing reagents of the present invention.

Referring now to the single FIGURE of the drawings, the apparatus of the present invention is seen basically to consist of a first chromatographic column 10 arranged in series with a second chromatographic column 11 followed by a conductivity cell 12, each item in turn being connected in series by liquid conduit means. Sample solution may be placed on or added to the column 10 in most any suitable manner as by transfer with a pipet followed by addition of solution of developing reagent from a beaker or pipet in a gravity flow system, but preferably, by means of a syringe (not shown) sample is added to the system at a sample injection valve 13. The sample injection valve 13 is preferably of a type commonly used for chromatographic analysis and typically is provided with a valve plug bore, or a loop of tubing connected to two of the valve body ports, which determines the sample size, i.e., volume, which is swept out by a steady stream of developing reagent as well understood in the art. In any event, the sample-holding void space is filled by a syringe or other convenient means after which the valve is manipulated to bring the sample-holding void into series with the stream of developing reagent constantly passing through a portion of the valve body and the selected sample portion is thereby swept on into the first of the chromatographic columns. Manageable amounts of sample solution handled by such valve and utilized according to the invention vary from about 0.002 to about 5 milliliters.

In the present apparatus, the sample injected at injection valve 13 is swept through the apparatus by solution of developing reagent 14, i.e., eluant solution, drawn from the reservoir 15 by pump 16 and passed through the sample injection valve 13 to the first chromatographic column 10. The solution leaving the chromatographic column 10, sometimes referred to as a separator column, with the cationic species resolved is conveyed by liquid conduit means to the second chromatographic column 11 wherein the metal ion species in the solution of developing reagent is precipitated and the anions of the solution of developing reagent are all exchanged for the anions of the form of the anion exchange resin in the column 11, these latter anions having also been utilized for the precipitation of the metal ion species of the developing reagent solution. The solution with resolved cation species therein are now stripped of the metal ions of the developing reagent then exits from the second chromatographic column 11 substantially free of other ionic species than the cations under determination and the counter valent anions picked up in the exchange in the second column 11. The second chromatographic column 11 charged with an anion exchange resin in a suitable form for precipitation of the metal ion of the developing reagent is sometimes referred to as a stripper column since it substantially frees the solution passing therethrough from all ion species except the cations under determination and their counter valent anions. The effluent from the second chromatographic column 11 is conveyed by liquid conduit means to a suitable detector such as a conductivity cell 12 wherein th resolved cationic species under determination are quantitatively detected. The electrical signal produced by the conductivity cell 12 is directed to the conductivity meter 17 and the output of the meter is directed to the recorder 18 or other suitable readout indicator, preferably a recorder-integrator.

The cation exchange resin 21 employed in the first chromatographic column 10 ordinarily does not require backwashing or regeneration since the resin is constantly being swept by the solution of developing reagent and remains in the form of the cation of that reagent. However, the anion exchange resin 22 in column 11 requires, periodically, either (1) replacement, or, (2) backwashing and regeneration to remove precipitated developing reagent and to place the resin in the proper anionic form. While it is not absolutely essential, it is convenient to provide valving such as multi-port valve 19 between the chromatographic column 10 and chromatographic column 11 to provide for the diversion and discard of regeneration or backwash liquid being passed through the column 11 as well as supplying regenerant solution. Likewise, it is convenient to provide a multi-port valve or equivalent valving such as valve 20 following chromatogrphic column 11 which provides for direction of effluent from the column to the detector 12 as well as for introduction of backwash liquid and, if desired, regenerant solution and further allows for the by-passing of the conductivity cell any time that operation of the conductivity cell is not required.

It must be understood that the chromatographic columns shown in the drawing are ordinarily small diameter tubing, usually of glass or stainless steel, the small diameter, together with fast flow rates of solution of developing reagent facilitating analysis times of generally less than about 20 to 30 minutes for a sample containing a plurality of ionic species, though somewhat longer time intervals are sometimes required. For the purposes of the present discussion and the appended claims, small diameter columns are those having an internal diameter (I.D.) of not more than about 3 millimeters. Larger diameter columns may be used if desired, such as columns having an I.D. of 25 or 50 millimeters, but with columns larger than about 10 millimeters I.D., i.e., analysis times are usually longer, and large amounts of sample, eluant solution and ion exchange resin are usually required. Therefore it is generally preferred for practice of the present invention in routine analytical work that the size of columns employed is in the range of about 2 to about 10 millimeters I.D., 2.8 millimeters I.D. and 9 millimeters I.D. being frequently used sizes.

In carrying out the present method, the sample size employed is preferably very small in order to facilitate rapid, sharp separation leading to more accurate determinations and especially to avoid overloading the cation exchange resin in the first column so that it is not necessary to employ large volumes of solution of developing reagent for the chromatographic separation in the separator resin bed, thus avoiding undue exhaustion of the anion exchange resin in the stripper bed.

The cation exchange resin used in this first bed, if a conventional resin, is employed in a small amount to provide a small total exchange capacity, but the resin is preferably a high performance, low capacity ion exchange resin. An example of a resin of this latter type is a surface sulfonated copolymer of styrene and divinylbenzene containing about 2 to about 4% by weight of divinylbenzene. The ion exchange capacity required in the second bed, that is the stripper bed, is by appropriate means than kept in manageable portions.

The amount of sample solution brought into the system as by sample injection valve 13 is generally in the range of about 0.002 to about 5 milliliters of a dilute solution containing a plurality of the cationic species to be measured, which in total are present in an amount, expressed in millliequivalents, not greater than about 1 to 10% of the ion exchange capacity of the separator bed, thus providing for good resolution on such column.

As indicated hereinabove, rather than using a gravity flow system, it is much preferred to use a pump and to supply a substantially continuous stream of developing reagnet according to good current chromatographic practice in which the solution of developing reagent is used to sweep the sample out of the sampling value and onto the column. Typical flow rates of eluant solution fall generally in the range of about 15 to 500 milliliters per hour of solution of developing reagent when the columns used are as large or larger than about 2.8 millimeters I.D., but smaller than about 10 millimeters I.D. The eluant solutions are used at a concentration in the range of about 0.001 to about 0.1 molar. Below about 0.001 molar concentration, the silver ion is too easily precipitated prematurely by traces of chloride, though the barium is not as likely to encounter trace sulfates and can often be used at a concentration as low as 0.0001 molar. Generally a concentration greater than about 0.10 molar is not needed to move alkaline earth metal cations of the column. Generally the most useful eluant concentration is in the range of about 0.005 to about 0.05 molar.

The ion exchange resin 21 to be used in the separator column, i.e., the column corresponding to column 10 of the drawing, is selected with a view to the kinds of cations to be separated and the developing reagent to be used therewith to achieve good separation. While any given separation may generally be achieved with any of several different resins, the most widely used gel type cation exchange resins commercially available such as Dowex 50 W ion exchange resin each require the use of a quantity of solution of developing reagent sufficient to rather rapidly exhaust most any of the standard resins usable herein in the stripper bed. Thus, it is must preferred as a practical matter and especially for purposes of regular repetitive analyses that the first, i.e., the separator, resin bed be charged with a resin having special characteristics. This special resin is one with high performance characteristics and ability to separate cationic species, but at the same time is a resin of low specific capacity so that only a small amount of developing reagent is needed to accomplish separation and elution off the resin bed. For the present purposes, it is preferred that the specific exchange capacity of the separator resin is in the range of about 0.005 to 0.1 milliequivalents per gram (meq/g) of resin.

The term high performance as used herein means that the ionic species are cleanly and sharply separated so that the readout means shows sharp concentration peaks and good baseline separation between all or most of the peaks, especially those of interest in a given analysis. This necessarily implies that the ionic species do not penetrate deeply into the resin structure nor are the ionic species otherwise held up during developing of chromatographic separation, else the peaks would not be sharp and well separated.

For high performance characteristic, it is essential that highly active ion exchange sites are disposed on and in a surface layer of the resin beads or particles and that such sites be readily and promptly available to ionic species in solution flowing over the resin bead surfaces. In cross-linked gel form ion exchange resin, the exchange process will not be as prompt and efficient as desired. Therefore, the preferred separator resin is pellicular in nature having the acitve sites at or vary close to the surfaces of the resin beads. Somewhat less preferred but superior to the gel particle resins are the more highly cross-linked ion exchange resins which are porous in nature having active sites along the walls of the pores but the pores providing far more accessibility to the ion species than is found in the gel type resins. The high performance resins facilitate obtention of the sharpest peaks and best resoltion of the ionic species although the other resins may be of advantage in a situation where two ion species tend to elute simultaneously from the high performance resin.

The preferred ion exchange resin for the separation of cations according to the present invention is a surface sulfonated copolymer of styrene and divinylbenzene having about 2 to 4% by weight divinylbenzene in the copolymer and the balance substantially styrens. The beads are preferably of an average particle size in the range of about 200 to about 400 mesh (U.S. Sieve Series) although finer sizes may be used if desired. In general, a coarser grade permits faster flow rates at a given applied pressure while finer grades afford greater exchange capacity per gram for a given degree of sulfonation. Surface sulfonation is accomplished rather simply by briefly heating the copolymer beads in hot, e.g., 80 to 100° C., concentrated sulfuric acid for a short time, for example, about 15 minutes or until the desired specific exchange capacity is achieved but not exceeded. A specific exchange capacity of about 0.02 meq/g of resin is sufficient to achieve good separations and is low enough to afford the use of a reasonable volume of regular resin in the stripper bed. In contrast, a conventional cation exchange resin has a specific exchange capacity of about 0.5 to 3 meq/g of water swollen resin.

The anion exchange resin 22 used in the stripper column is preferably a high capacity resin so that the resin can handle relatively large volumes of solution of developing reagent, for example, not only the solution needed for the analysis of a single sample but preferably a plurality or multiplicity of samples, preferably at least 5 samples and much more preferably at least 20 samples without allowing the metal ion of the developing reagent to reach the conductivity cell. Any of the commercially available high capacity ion exchange resins is usable in the stripper column, gel type resins being preferred. In the stripper column, that is the second chromatographic column 12 in the drawing, the anion exchange resin employed is in an appropriate form for precipitation of the metal ion being used in the developing reagent solution. When using a solution of silver nitrate as developing reagent the stripper resin is in the chloride form. When using barium chloride as the developing reagent, the stripper resin is in the sulfate form. The counter valent ion of the silver ion or barium ion used as the developing reagent need not necessarily be nitrate or chloride ion respectively, but may be a compatible ion in the present system which provides a soluble developing reagent salt and also does not precipitate the cations to be analyzed.

On steadily eluting sample cations of interest from the separator column with silver nitrate solution according to the invention, the separated cations and silver nitrate enter the stripper column charged with an anion exchange resin in the chloride form. The silver ions react with the chloride ions from the active sites and silver chloride is substantially all precipitated, though efficiency of precipitation drops off somewhat from nearly 100 percent as the column approaches exhaustion. The nitrate ions which were counter valent with the silver ions are captured at the ion exchange sites once holding chloride ions so that substantially only the chlorides of the cations of interest move off the anion exchange resin, regardless of the anion species in the relatively small sample tested.

In the event the sample solution contains an acid having a dissociation constant greater than about $1 \times 10^{-6}$ the acid anion is exchanged for chloride ions in the stripper column and the hydrogen or hydroium ions are quickly passed through both columns ahead of most cations and well separated therefrom.

Similarly on using a solution of barium chloride as developing reagent and a sulfate form anion exchange resin in the stripper column, the barium is substantially precipitated as barium sulfate and chloride ions are captured at the anion exchange sites so that substantially only sulfates are eluted from the stripper column. Acid species in the sample solution are promptly eluted off the separator column and the anions thereof exchanged for sulfate ions in the stripper column whereby $H_2SO_4$ and/or $HSO_4^-$ are eluted from the second column and move to the detector ahead of most other cations and their counter valent anions.

Sample solutions that are slightly alkaline do not interfer noticeably by precipitating silver ions or barium ions, but more strongly alkaline samples tend to casue precipitation, especially of silver ions, and markedly alkaline solutions are best neutralized to about pH 8.5 or less or sufficiently to avoid precipitating the metal ion of the developing reagent.

Regeneration of the stripper column containing sulfate ion form anion exchange resin, exhausted by precipitation of the highly insoluble barium sulfate, cannot be carried out as a practical matter and the resin must generally be discarded unless the resin and precipitate are successfully separated on suspending one solid and not the other.

Regeneration of the stripper column containing chloride form anion exchange resin exhausted by precipitation of silver chloride is carried out by washing the resin with aqueous ammonium chloride — ammonium hydroxide solution containing, e.g., about 5 to 15% by weight $NH_4Cl$ and $NH_4OH$, dissolving the silver ion and placing the anion exchange resin back in the chloride form, after which the resin is washed with distilled or de-ionized water until the effluent is substantially free of ionic materials.

Sample solutions containing substantial amounts of chloride salts to be analyzed using silver nitrate eluant or sulfate salts to be analyzed using barium chloride as eluant should be studied to determine the necessity or desirability of using such respective eluants, all factors considered, and if no change in eluant solution is to be made, the sample solutions are preferably pretreated by passing them through an anion exchange resin in the nitrate form.

The ion exchange resins usable in the stripper column, i.e., the second column, are, typically, polystyrene or modified polystyrene copolymers cross-linked, e.g., with divinylbenzene, and carrying nuclear groups, the latter providing the active exchange sites. The strong base anion exchange resins carry nuclear chloromethyl groups which have been quaternized. Other usable anion exchange resins are the polyalkylenepolyamine condensates.

For further information on ion exchange theriory, processess and resin synthesis, reference is made to the monograph "Dowex": Ion Exchange" 3rd Ed., 1964, published by the Dow Chemical Company, Midland, Michigan, and the two volume work "Ion Exchange" edited by Jacob A. Marinsky and published by Marcel Dekker Inc., New York 1966. Chapter 6, Vol. 2 of "Ion Exchange" is devoted to a description of synthesis of ion exchange resins of various types usable herein in the stripper resin bed.

The ionic species reaching the detector do not elicit equally great responses per equivalent weight of ion, e.g., the conductance of 0.01 molar $CaCl_2$ solution is not the same as the conductance of 0.01 molar $MgCl_2$ solution, nor is either the same as for 0.01 molar $KCl$ solution. Therefore the instrumental response of the present instrument must be calibrated using known concentrations of known substances in order to obtain accurate quantitative analyses.

The detector used must be able to determine the presence of each ion of interest and the quantity thereof by response to some physical property of the ions in water solution. While the detector may be most any of a polarographic cell, a differential refractometer, a specific ion electrode or a spectrophotometer, these generally lack the sensitivity, selectivity, simplicity, ruggedness and universality of the conductivity cell, and for practical purposes, the latter is usually a clear choice over all the other types of detectors.

EXAMPLES

The following examples serve to illustrate the use of the method and apparatus of the invention and the scope of the invention is not intended to be limited thereto.

EXAMPLE 1

A 2.8 × 300 mm column was filled with a surface sulfonated styrene divinylbenzene copolymer having a specific ion exchange capacity of 0.0159 meq/g. This separating column was coupled to a 2.8 × 300 mm stripper column which contained a commercial anion exchanging material Dowex 1 × 8 ion exchange resin in the chloride ion form. The separating column was further provided with a sample injection valve, pump and eluant reservoir while the effluent from the stripper column was directed to a conductivity cell and readout means. A 0.1 ml sample of an aqueous solution containing 10 parts per million (ppm) of magnesium ion and 21 ppm calcium ion was injected onto the column and elution carried out with a 0.05 N aqueous silver nitrate solution at a flow rate of 80 ml./hr. The magnesium ion was sharply separated from the calcium ion and eluted after about 3.25 minutes, the calcium being eluted at about 4.75 minutes.

Further elutions of varying and known concentrations of the calcium and magnesium ions showed the height of the eluted conductivity peaks to be approximately proportional to the concentrations of the respective ions in the injected samples.

EXAMPLE 2

A 2.8 × 300 mm column was filled with a surface sulfonated styrene divinylbenzene copolymer having a specific ion exchange capacity of 0.024 meq/g. This separating column was coupled to a stripper column 9 × 300 mm filled with Dowex 1 × 8 ion exchange resin chloride form. An aqueous solution of 0.05 N $AgNO_3$ was used as eluant at a flow rate of 92 ml./hr.

A number of 0.1 ml samples of water taken from various locations in a local river were injected and eluted in the manner of Example 1. The concentrations of calcium and magnesium in each sample was determined by measuring the height of the eluted peaks. These same samples were analyzed for calcium and magnesium by atomic absorption which is a well-known and accepted analytical technique. The agreement between the results obtained by the method described herein and by the atomic absorption method was very satisfactory as seen in the following table of comparison:

| Sample No. | PPM of Calcium In Sample | | PPM of Magnesium In Sample | |
|---|---|---|---|---|
| | By Method Described Herein | By Atomic Absorption | By Method Described Herein | By Atmoic Absorption |
| 1 | 46 | 47 | 13 | 12 |
| 2 | 74 | 74 | 21 | 19 |
| 3 | 47 | 49 | 14 | 12 |
| 4 | 53 | 56 | 15 | 13 |

What is claimed is:

1. Apparatus for chromatographic quantitative analysis of a plurality of species of cations in aqueous sample solution, which comprises:
   a first chromatographic column for separating the cationic species, said first column being charged with a cation exchange resin;
   means for adding sample solution and solution of developing reagent to the first chromatographic column;
   a second chromatographic column for precipitating metal ions contained in said developing reagent, said second column being charged with an anion exchange resin in a form selected from the chloride form and the sulfate form, the anion exchange resin having a total exchange capacity at least 50 times that of the cation exchange resin;
   liquid conduit means for conveying effluent from the first column to the second column;
   a common detector means for quantitatively detecting each separated cation species of interest exiting from said second column;
   and liquid conduit means for conveying effluent from said second column to said common detector means.

2. The apparatus as in claim 1 in which the common detector means is a conductivity cell and associated readout means.

3. The apparatus as in claim 1 in which the columns are cylindrical and have an inside diameter not exceeding about 10 millimeters.

4. The apparatus as in claim 1 in which the cation exchange resin is surface sulfonated copolymer of styrene and divinylbenzene containing about 2 to 4 percent by weight divinyl benzene.

* * * * *